United States Patent
Di Nardo et al.

(10) Patent No.: US 8,750,969 B2
(45) Date of Patent: Jun. 10, 2014

(54) WEARABLE VISION DEVICE

(75) Inventors: Francesco Di Nardo, Rome (IT); Alessandro Moro, Rome (IT); Sandro Pelo, Rome (IT)

(73) Assignee: Pierrel Pharma SRL, Capua (CE) (IT)

( * ) Notice: Subject to any disclaimer, the term of this patent is extended or adjusted under 35 U.S.C. 154(b) by 52 days.

(21) Appl. No.: 13/577,652

(22) PCT Filed: Feb. 16, 2011

(86) PCT No.: PCT/IB2011/050642
§ 371 (c)(1),
(2), (4) Date: Oct. 8, 2012

(87) PCT Pub. No.: WO2011/101789
PCT Pub. Date: Aug. 25, 2011

(65) Prior Publication Data
US 2013/0046183 A1 Feb. 21, 2013

(30) Foreign Application Priority Data
Feb. 16, 2010 (IT) .............................. RM2010A0061

(51) Int. Cl.
*A61B 6/00* (2006.01)
*F21V 9/16* (2006.01)
(52) U.S. Cl.
USPC ...................................... 600/476; 250/458.1
(58) Field of Classification Search
USPC .................. 600/178, 476; 351/206, 221, 497; 250/216, 458.1, 459.1
See application file for complete search history.

(56) References Cited

U.S. PATENT DOCUMENTS
2003/0173525 A1 9/2003 Seville

OTHER PUBLICATIONS

PCT Search Report for International Application PCT/IB2011/050642 filed on Feb. 16, 2011 in the name of Universita' Cattolica Del Sacro Cuore. Mail date: Apr. 28, 2011.
PCT Written Opinion for International Application PCT/IB2011/050642 filed on Feb. 16, 2011 in the name of Universita' Cattolica Del Sacro Cuore. Mail date: Apr. 28, 2011.
Lane PM, Gilhuly T, Whitehead P, Zeng H, Poh CF, Ng S, Williams PM, Zhang L, Rosin MP, MacAulay CE "Simple device for the direct visualization of oral-cavity tissue fluorescence". J Biomed Opt. Mar.-Apr. 2006 11(2):024006.
Parkin DM, Bray F, Ferlay J, Pisani P. Global cancer statistics, 2002. CA Cancer J Clin 2005, 55:74-108.
Poh CF, Zhang L, Anderson DW, et al. "Fluorescence visualization detection of field alterations in margins of oral cancer patient". Clin Cancer Res 2006. 12:6716-22.
Rahman M, Chaturvedi P, Gillenwater AM, Richards-Kortum R "Low-cost, multimodal, portable screening system for early detection of oral cancer". J Biomed Opt. May-Jun. 2008 13(3):030502.
Svistun et al.: "Vision enhancement system for detection of oral cavity neoplasia based on autofluorescence", Head & Neck, Mar. 31, 2004, pp. 205-215.
Westra, W. H. et al. "Fluorescence Visualization in Oral Neoplasia: Shedding Light on an Old Problem" Commentary on Poh et al. Clin Cancer Res 2006. 12(22) Nov. 15, 2006; 6594-7.

*Primary Examiner* — Michael Rozanski
(74) *Attorney, Agent, or Firm* — Steinfl & Bruno LLP

(57) ABSTRACT

The present invention aims to provide alternative means for the diagnosis of the risk of developing mouth mucosa cancers by means of fluorescence, easy to use, simple, light and space-saving and diagnostic kits comprising the above-mentioned device.

13 Claims, 4 Drawing Sheets

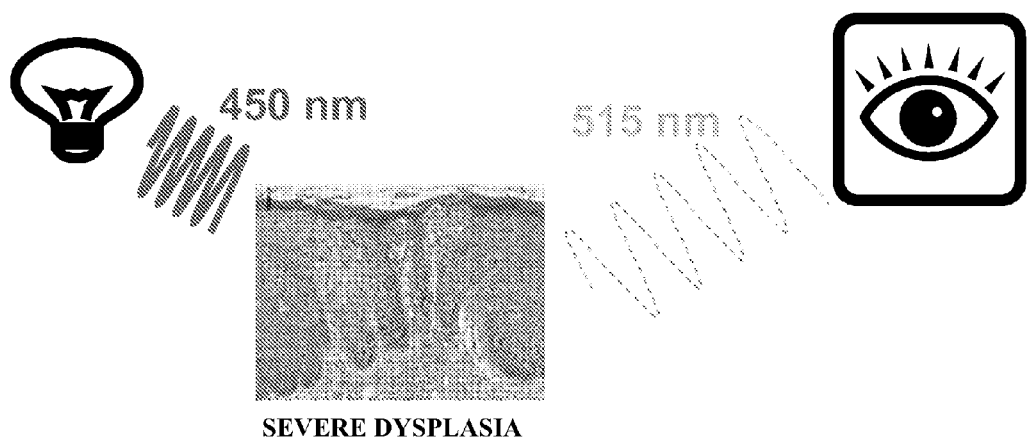
Fig. 1
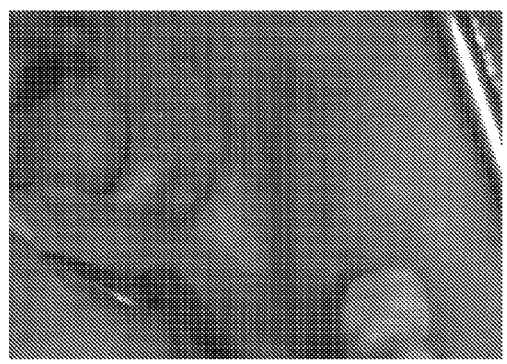 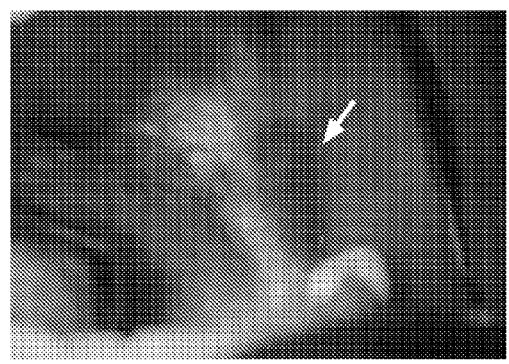
Fig. 2A Fig. 2B

WEARABLE VISION DEVICE

CROSS REFERENCE TO RELATED APPLICATIONS

The present application is the US national stage of International Application PCT/IB2011/050642 filed on Feb. 16, 2011, which, in turn, claims priority to Italian Patent Application RM2010A000061 filed on Feb. 16, 2010.

PRIOR STATE OF ART

Oral carcinoma has, in the world, an incidence of 8.2 cases out of 100000 male inhabitants per year and of 2.8 cases out of 100000 female inhabitants per year. However, in the world some areas are more affected; in the Indian Subcontinent the oral carcinoma exceeds 30% of all tumours. More than 90% of these tumours are classified as "squamocellular tumour" (Parkin D M, Bray F, Ferlay J, Pisani P. *Global cancer statistics*, 2002. CA Cancer J Clin 2005, 55:74-108).

The occurrence age is placed between the VI and the VII life decade; however, during the last decades, an increase in the cases of oral carcinoma in young age with prevailing lingual localization has been found.

Smokers have a risk of death due to oral cavity cancer 5 times higher than the remaining population. Even the excessive alcohol consumption promotes the oral cavity cancer and the association of alcohol and tobacco smoke has a synergic effect upon the increase in the risk of developing the tumour.

Some importance from the aetiological point of view seems to have also poor oral hygiene, incongruous prostheses, defective dental reconstructions, dental archs in wrong occlusion, sharp cusps. Frequently viral DNA (HPV, HCV) has been found in the oral cavity carcinoma. The identification of all lesions defined "precancerous", such as leukoplakia, eritroplakia and lichen planus, appear to be particularly important for the preventive purpose, as they constitute a specific risk factor. According to the literature data, le precancerous lesions can change into carcinoma in an amount variable between 5 and 18% of the cases.

Up to now no competent organism has ever proposed to establish screenings on wide populations. However, the study of the groups at risk could be useful for preventive purposes.

Currently the recommended screening tests are the clinical examination and the application of Toluidine blue on the suspected lesion, followed by definitive diagnosis with incisional or excisional biopsy.

Toluidine blue is the most used test; however id shows false negatives and the area wherein the dye is fixed seems not to always correspond to the real neoplasia extension; for this reason promising techniques of secondary prevention of the oral cavity cancer, based upon optical apparatuses are under development (W. H. Westra D. Sidransky "*Fluorescence Visualization in Oral Neoplasia: Shedding Light on an Old Problem*" Commentary on Poh et al. Clin Cancer Res 2006; 12(22) Nov. 15, 2006; 6594-7; Poh C F, Zhang L, Anderson D W, et al. "*Fluorescence visualization detection of field alterations in margins of oral cancer patient*". Clin Cancer Res 2006; 12:6716-22).

The diagnosis performed by using optical apparatuses is based on the evidence that some tissues emit fluorescence when lighted by visible light. This phenomenon is known as "autofluorescence". The tissues' autofluorescence provides diagnostically relevant data for preventing tumours in the lung, in the cervix uteri, in the skin and in the oral cavity.

The light interaction with the tissue reveals changes in the structure and in the metabolic activity in areas wherein there is clonal activity. More precisely, the loss in autofluorescence seems to reflect complex remodellings such as rupture of the tissue collagen, neoangiogenesis and decrease in the flavin adenine dinucleotide (FAD concentration) in the oxidized form thereof.

The healthy oral mucosa emits a small fluorescence with pale green colour (515 nm) when lighted by blue-violet light (450 nm).

In the dysplastic tissues the autofluorescence appears reduced basically due to alterations of the cellular metabolism (the FAD concentration decreases in the cells with active cellular metabolism) and scattering effect due to alterations of the cellular structure and disarranging of the extracellular matrix.

When the oral mucosa has suffered biochemical and/or structural alterations (squamous hyperplasia, dysplasia, carcinoma), an area of decreased autofluorescence can be seen.

A publication of the Journal of Biomedical Optics in 2006 showed a device able to highlight the decrease in fluorescence, indicating cancer degeneration in the area under examination (Lane P M, Gilhuly T, Whitehead P, Zeng H, Poh C F, Ng S, Williams P M, Zhang L, Rosin M P, MacAulay C E "*Simple device for the direct visualization of oral-cavity tissue fluorescence*" J Biomed Opt. 2006 March-April; 11(2): 024006, FIG. 1). The device consisted in a light source connected by means of an optical fibre cable to the portion of the tool to hold. In the latter the light firstly crossed an excitation filter, after a converging lens, subsequently a dichroic mirror and at last it hit the oral mucosa. From the oral mucosa, the light subsequently travelled a backward route through the dichroic mirror. However, this time it was directed toward the examiner eye after having crossed two filters: the first emission filter, the second contrast filter.

The same magazine in May 2008 published a work about a new device based on the same principle: improvements are provided by the transportability, by the binocular vision and by the association to video recording system (Rahman M, Chaturvedi P, Gillenwater A M, Richards-Kortum R "*Low-cost, multimodal, portable screening system for early detection of oral cancer*" J Biomed Opt. 2008 May-June; 13(3): 030502)

The device available in the state of art, as briefly described above, needs the use of a complex optical apparatus, constituted by several portions, which has to be held by the operator performing the analysis.

Such device allows visualizing the decrease in autofluorescence of diagnostic interest in the oral mucosa of the examined patients and it allows, with the last introduced changes published in 2008 (Rahman et al 2008, above) a binocular vision and the recording of the visualized images by means of an extremely complex device which has to be worn by the operator.

SUMMARY OF THE INVENTION

The present invention aims to simplify, and therefore to make more accessible to the operators, the early diagnosis of the precancerous lesions of the oral cavity by means of the autofluorescence examination. The complexity of the device shown in the publication of Rahman et al 2008 does not allow a use thereof on wide scale which could be useful for the mass prevention screening.

Although compared to the device published in 2006 the one of 2008 has allowed a binocular vision and a direct wearability of the same, that frees the operator's hands, the device appears clearly complex, expensive and not suitable for immediate use. Not lastly, the space requirement of such device and the need for spaces to place back the same further complicate the device versatility. Furthermore, such device has a not irrelevant weight for the operator which allows a limited wearability thereof and which limits the motion of the operator's head.

The whole system weighs about 1.5 kilograms and consists of a small helmet device, with integrated LED surgical light, surgical binoculars and an integrated CCD photo/video camera and an integrated power supply battery.

The technical principle linked to the device available in the state of art is to provide a highly selective lighting, in terms of wavelength, of the portion to be analysed so as to excite precisely the fluorophores of diagnostic interest. The device is equipped with lowpass filters to filter the emission.

The present invention wants to provide alternative means for the early diagnosis of the precancerous and cancerous lesions of the oral mucosa by the observation of the autofluorescence, easy to use, simple light and space-saving.

The present inventors have thought to make a device allowing also the use of means usually present in a dental laboratory, that is a photopolymerization lamp, hence a lamp emitting a light usually comprised in a wavelength range from about 400 to about 500 nm, by adapting the features of the diagnostic device to means usually used in odontology, by allowing at the same time the reduction of the costs for the users, the decreasing of the space requirement to store the device, a higher wearability of the same that enables the operator to move better and allowing nevertheless a binocular vision and, optionally, the possibility to record and/or photograph the images by means of additional devices.

The additional devices will be usual apparatuses for recording images, such as digital and non digital cameras and photo or video cameras on which a filter constituted by a lens having the same features as the one mounted on the eyeglasses of the present description can be mounted.

The invention hence provides an alternative solution to the known art solving also some negative features listed above, by providing a highly selective lens which can be used with simple photopolymerizing lamps, that are usually found in dental laboratories and consulting rooms.

The system according to the present invention enables to exploit a photopolymerizing lamp as light source for the analysis of the autofluorescence tissue response as described above, as it provides a wearable device as defined in claim 1.

An optical filter system according to claim 9 is also an object of the present invention.

The present invention further relates to a kit comprising a device according to the present description and one or more writing devices using an ink comprising a fluorescent or non fluorescent dye, which can be detected through said device; a kit comprising a device according to the present description and one or more optical filter systems according to the present description optionally mounted on adapters for video/photographic recording apparatuses.

A kit comprising a device according to the present description and one or more writing devices using an ink comprising fluorescent or non fluorescent dye, which can be detected through said device and one or more optical filter systems according to the present description optionally mounted on adapters for video/photographic recording apparatuses.

BRIEF DESCRIPTION OF THE FIGURES

FIG. 1 shows a schematization of the diagnostic principle based on the autofluorescence detection described above in the state of art.

FIG. 2 shows an example of the detection obtained with the device of the present description, in the 2A the examined oral mucosa is lighted by normal light, box 2B shows the decrease in autofluorescence detected with the device of the invention on the same oral mucosa lighted by photopolymerizing lamp, the arrow points the clear decrease in autofluorescence, associated to the risk of neoplasia.

GLOSSARY

Figure 3:
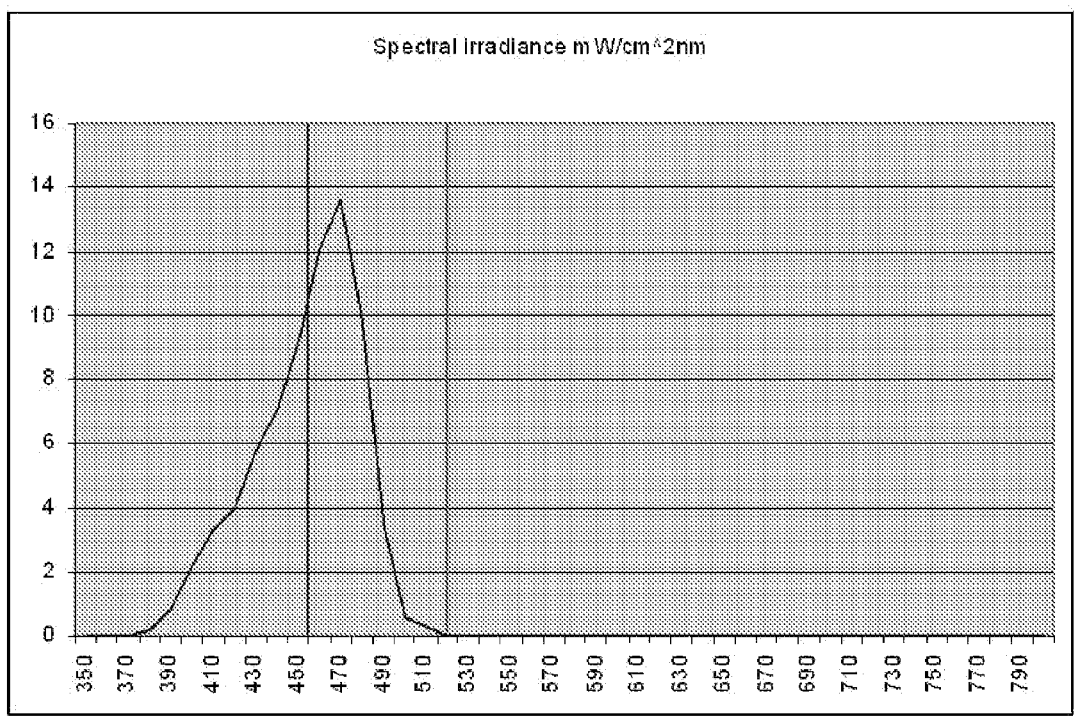
FIG. 3 is a graph showing the radiation spectrum of a halogen lamp emitting light for photopolymerization (in $mW/cm^2$-nm); the values in abscissa are expressed in nanometers; 450 nm is the wavelength requested to excite the oxidized FAD; 515 nm is the wavelength emitted by the excited oxidized FAD.

Canada balsam (or *Canada turpentine*, or balsam of fir) is a turpentine obtained from the resin of the balsamic fir (*Abies balsamea*). The resin, dissolved in essential oils, is a colourless, viscous and adhesive liquid which dries up in a transparent mass. Due to its refraction index (n=1.55) similar to that of the Crown glass, the purified and filtered Canada balsam has had a traditional use as wholly transparent adhesive (once dried up) for glasses, lenses and optical components.

Optical glass is the material used to produce quality objectives for its transparency and for its refractive properties. The addition of elements like barium, boron, phosphorous, lanthanum allows obtaining glasses with low or high refraction and high or low dispersion. The optical glass is produced by making the raw material to melt and then to slowly cool down.

Photopolymerizing lamp photopolymerisator or "curing light" consists in a light source, such as a halogen lamp or LED, used by the odontologists to make the resins, commonly used to fill up cavities or dental roots, to solidify. The light emitted by the photopolymerizing lamps is generally comprised in an emission spectrum of 380-500 nm.

The term "Dysplastic/anaplastic lesions of the oral cavity" means the mucosa areas of the oral cavity, characterized by the presence of the alterations of the normal cellular composition or of the normal cellular proliferation which affect the tissue structure and which can lead to a cancerous disease (in case of dysplasia) or they are themselves the anatomo-pathological sign of the presence of a tumour (in case of anaplasia).

With "Animal biological tissue" it is meant a complex and dynamic material of animal origin constituted by cells that, together with their basic substances (extracellular matrix), act together in a coordinated way to carry out a particular function in reply to specific stimuli, where the meaning of animal is of complex (pluricellular) organisms belonging to the animal kingdom, in particular mammals including humans.

With "Frame for glasses" it is meant any structure suitable to mount lenses, apt to be worn so that the lenses are positioned in front of the user's eyes.

DETAILED DESCRIPTION OF THE INVENTION

FIG. 1 schematizes the autofluorescence principle underlying the present invention.

In particular, it can be noted that the healthy oral mucosa emits a light fluorescence with pale green colour (515 nm) when lighted by blue-violet light (450 nm).

In the dysplastic tissues the autofluorescence appears reduced substantially due to alterations of the cellular metabolism (the FAD concentration decreases in the cells with active cellular metabolism) and scattering effect due to alterations of the cellular structure and disarranging of the extracellular matrix.

If the oral mucosa has undergone biochemical and/or structural alterations (squamous hyperplasia, dysplasia, carcinoma), an area of decreased autofluorescence is noted, as highlighted in the following FIGS. 2A and 2B.

A wearable device according to the present invention allows the detection of the autofluorescence of an animal biological tissue emitting a fluorescent component having a wavelength of about 515 nm when lighted by a light source at a wavelength comprised between 200 and 1.100 nm, provided that it comprises at least a component between 400 and 500 nm, preferably 450 nm.

Such animal biological tissue could be selected among the tissues commonly known to the person skilled in the art showing a decrease in autofluorescence at about 515 nm when lighted by a light source as described above, in presence of dysplastic/anaplastic lesions, such as for example, the pulmonary tissue, the cervix uteri and the oral cavity mucosa.

For example, the person skilled in the is aware that the fluorophore flavin adenine dinucleotide (FAD), in its oxidized form responds to a light of 450 nm (blue-violet) by emitting a fluorescence having a wavelength of 515 nm (green).

In the tumour tissue, the fluorescence of the oxidized FAD irradiated by blue-violet light decreases. The cause of this phenomenon is not known with certainty: probably it has to be searched for in a combination of several phenomena. The tumours are generally associated to angiogenesis which could lead to an increase in the absorption of the exciting light (the haemoglobin strongly absorbs the light at 420 nm). Even the consequent disarranging of the extracellular matrix and the epithelial thickening caused by the tumour seem to decrease the signal intensity. The cross-links bounds of the collagen matrix seem to be subjected to the same phenomenon of absorption, excitation and emission of a luminous signal.

Consequently, any tissue showing these features could be investigated with the device of the present invention.

The device according to the present invention isolates the light around 515 nm (the one emitted by the oxidized FAD).

The light source which can be advantageously used can be a photopolymerizing lamp of the type commonly used by the odontologists, emitting a light having a peak generally comprised between 440 and 480 nm, the absorption curve of the composites used by the odontologists being between 360 and 520 nm with a peak at 465 nm. In particular, it is essential that the light source emits also at wavelengths near to the one at which the oxidized FAD excites (450 nm). Consequently, the light emitted by the photopolymerizing lamp is suitable to produce autofluorescence of the animal biological tissue under examination.

A not limitative list of light sources suitable to the operation with the present invention is shown in Table 1 of the EXAMPLES.

FIG. 3 is a graph showing the radiation spectrum of a halogen lamp emitting light for photopolymerization (in mW/cm$^2$-nm); the values in abscissa are expressed in nanometres; 450 nm is the wavelength requested to excite the oxidized FAD; 515 nm is the wavelength emitted by the excited oxidized FAD.

According the preferred embodiment, the device according to the present invention comprises a system of optical filter of bandpass type, so as to isolate the fluorescent component (515 nm) and substantially excluding other light components in the visible and in the UV.

The optical filter system according to the present invention hence guarantees a specificity for the fluorescence of the oxidized FAD excluding the blue light, the red light and the UV rays and having a transparency peak of about 515 nm (corresponding to the light emitted by the oxidized FAD).

Figure 4:
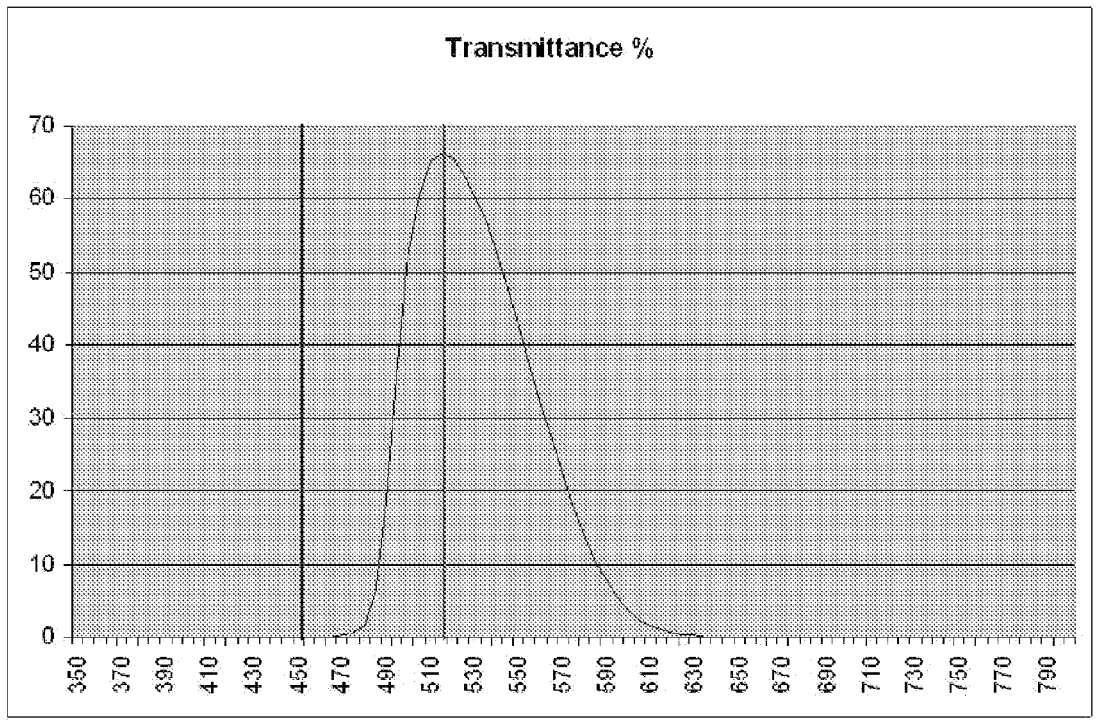
FIG. 4 is a graph representing the transmittance curve desired for a filter according to the present invention; the values in abscissa are expressed in nanometers; 450 nm is the wavelength requested to excite the oxidized FAD; 515 nm is the wavelength emitted by the excited oxidized FAD.

FIG. 4 is a graph representing the transmittance curve wished for a filter according to the present invention; the values in abscissa are expressed in nanometres; 450 nm is the wavelength requested to excite the oxidized FAD; 515 nm is the wavelength emitted by the excited oxidized FAD.

The optical filter system according to the present invention can be carried out for example by coupling several superimposed nanometre-controlled lenses (at least two). In particular the system can comprise three lenses in optical glass. Preferably, lenses in optical glass having the following features, respectively, can be used:

1) bandpass filter having a transmittance curve showing a peak at about 500 nm and a bandwidth comprised between about 300 and 700 nm;

2) highpass filter having a transmittance curve showing a plateau beyond about 540 nm;

3) bandpass filter having a transmittance curve showing a peak at about 465 nm and a bandwidth comprised between about 300 and 600 nm.

A non limitative example of commercial filters of this type is given by the filters in optical glass Schott BG39, GG495 and BG23.

Preferably, the filters are worked in a plane-parallel way, optically polished on the two surfaces and glued to each other with a suitable gluing agent, for example the synthetic Canada balsam or any other gluing agent having similar technical features, known to the person skilled in the art.

Of course, it is to be meant that the order according to which the lenses are superimposed and coupled will not modify the final result.

Table 2 reported in the chapter EXAMPLES shows the technical features of an optical filter system according to a preferred embodiment of the present invention.

The optical filter system, in particular the lenses by which it is constituted, can be advantageously modelled and housed inside any frame for glasses or visor.

The glasses' frame can comprise any wearing system (pince-nez, laces, small rods, etc.) preferably adjustable for a good adhesion to the operator's face.

The frame can further comprise shielding members, for example side small tabs or around the lenses in order to allow the insulation with respect to the environmental light.

Advantageously, the device according to the present invention could be made even in the form of additional lenses (clip-on type) apt to be applied for example to a pair of glasses for sight correction.

The device may further comprise video recording means, arranged so as to capture images filtered by the optical filter system.

For example such recording means could comprise a micro camera to record the same images which the operator sees through the filter lenses.

According to the present invention, it is also possible to provide a diagnostic kit comprising a device as herein described and a writing device using an ink comprising a fluorescent or a non fluorescent dye, which can be detected through said device.

The writing device will preferably be a dermatological pen which may be provided in sterile packagings, advantageously of disposable type. Obviously the ink and the selected dye will be of the type suitable to surgery in general. The pen could be sterilized for example by gamma rays. Obviously, the ink will be not toxic and resistant to the pre-surgical treatment, of the type known to the person skilled in the art and it will include, besides a conventional dye, visible to the naked eye, a fluorescent dye which emits fluorescence at a wavelength comprised between about 500 nm and about 550 nm.

This will allow the operator to define the areas of interest during the visualization with the device of the invention and to be able to visualize the delimitation carried out even under environmental lighting conditions, with naked eye.

In a preferred embodiment, such dye will emit the desired fluorescence when lighted by light containing components between about 400 and about 500 nm. The person skilled in the art will easily be able to select the suitable dye by evaluating the dyes known in literature.

A not limiting example of known commercial dyes which emit at the wished wavelength when excited by a light containing components between about 400 nm and about 500 nm is reported in table 3 below.

TABLE 3

| | | |
|---|---|---|
| DiO | 487 nm | 501 nm |
| LysoSensor Green pH 5.0 | 447 nm | 502 nm |
| Cy 2 | 489 nm | 503 nm |
| LysoSensor Green | 447 nm | 504 nm |
| Fura-2, high Ca | 336 nm | 504 nm |
| Fura-2 Ca2+ | 336 nm | 505 nm |
| SYTO 13-DNA | 488 nm | 506 nm |
| YO-PRO-1-DNA | 491 nm | 507 nm |
| YOYO-1-DNA | 491 nm | 509 nm |
| eGFP (Enhanced Green Fluorescent Protein) | 488 nm | 509 nm |
| LysoTracker Green | 503 nm | 509 nm |
| GFP (S65T) | 489 nm | 509 nm |
| BODIPY FL, MeOH | 502 nm | 511 nm |
| Sapphire | 396 nm | 511 nm |
| BODIPY FL conjugate | 503 nm | 512 nm |
| MitoTracker Green | 490 nm | 512 nm |
| MitoTracker Green FM, MeOH | 490 nm | 512 nm |
| Fluorescein 0.1M NaOH | 493 nm | 513 nm |
| Calcein pH 9.0 | 494 nm | 514 nm |
| Fluorescein pH 9.0 | 490 nm | 514 nm |
| Calcein | 493 nm | 514 nm |
| Fura-2, no Ca | 367 nm | 515 nm |
| Fluo-4 | 494 nm | 516 nm |
| FDA | 495 nm | 517 nm |
| DTAF | 495 nm | 517 nm |
| Fluorescein | 495 nm | 517 nm |
| Fluorescein antibody conjugate pH 8.0 | 493 nm | 517 nm |
| CFDA | 495 nm | 517 nm |
| FITC | 495 nm | 517 nm |
| Alexa Fluor 488 hydrazide-water | 493 nm | 518 nm |
| DyLight 488 | 493 nm | 518 nm |
| 5-FAM pH 9.0 | 492 nm | 518 nm |
| FITC antibody conjugate pH 8.0 | 495 nm | 519 nm |
| Alexa 488 | 493 nm | 520 nm |
| Rhodamine 110 | 497 nm | 520 nm |
| Rhodamine 110 pH 7.0 | 497 nm | 520 nm |
| Alexa Fluor 488 antibody conjugate pH 8.0 | 499 nm | 520 nm |
| BCECF pH 5.5 | 485 nm | 521 nm |
| PicoGreen dsDNA quantitation reagent | 502 nm | 522 nm |
| SYBR Green I | 498 nm | 522 nm |
| Rhodaminen Green pH 7.0 | 497 nm | 523 nm |
| CyQUANT GR-DNA | 502 nm | 523 nm |
| NeuroTrace 500/525, green fluorescent Nissl stain-RNA | 497 nm | 524 nm |
| Dansyl Cadaverine | 335 nm | 524 nm |
| Rhodol Green antibody conjugate pH 8.0 | 499 nm | 524 nm |
| Fluoro-Emerald | 495 nm | 524 nm |
| Nissl | 497 nm | 524 nm |

TABLE 3-continued

| | | |
|---|---|---|
| Fluorescein dextran pH 8.0 | 501 nm | 524 nm |
| Rhodamine Green | 497 nm | 524 nm |
| 5-(and-6)-Carboxy-2',7'-dichlorofluorescein pH 9.0 | 504 nm | 525 nm |
| Dansyl Cadaverine, MeOH | 335 nm | 526 nm |
| eYFP (Enhanced Yellow Fluorescent Protein) | 514 nm | 526 nm |
| Oregon Green 488 | 498 nm | 526 nm |
| Oregon Green 488 antibody conjugate pH 8.0 | 498 nm | 526 nm |
| Fluo-3 | 506 nm | 527 nm |
| BCECF pH 9.0 | 501 nm | 527 nm |
| SBFI-Na+ | 336 nm | 527 nm |
| Fluo-3 Ca2+ | 506 nm | 527 nm |
| Rhodamine 123, MeOH | 507 nm | 529 nm |
| FlAsH | 509 nm | 529 nm |
| Calcium Green-1 Ca2+ | 506 nm | 529 nm |
| Magnesium Green | 507 nm | 530 nm |
| DM-NERF pH 4.0 | 493 nm | 530 nm |
| Calcium Green | 506 nm | 530 nm |
| Citrine | 515 nm | 530 nm |
| LysoSensor Yellow pH 9.0 | 335 nm | 530 nm |
| TO-PRO-1-DNA | 515 nm | 531 nm |
| Magnesium Green Mg2+ | 507 nm | 531 nm |
| Sodium Green Na+ | 507 nm | 531 nm |
| TOTO-1-DNA | 514 nm | 531 nm |
| Oregon Green 514 | 512 nm | 532 nm |
| Oregon Green 514 antibody conjugate pH 8.0 | 513 nm | 533 nm |
| NBD-X | 466 nm | 534 nm |

The advantage conferred by the writing device of the herein described kit is given by the fact of allowing the operator to circumscribe the areas with reduced autofluorescence and therefore potentially dysplastic/neoplastic areas, in order to allow the removal of the same, by keeping on the detection device and thus by visualizing in a precise way the above-mentioned areas.

The used normal pre-surgical writing devices are generally constituted by dyes, the visualization of which is not quite easy, if not impossible, with the invention device. The dermatological pen herein described, hence, adds a practical advantage for the operator in the diagnosis for autofluorescence described above.

Alternatively, or in addition, the kit of the present invention, could contain, apart from the device, an optical filter system of the invention, which the operator could model according to the needs thereof to adapt, for example, to the wished image recording systems. The operator, then, may model the herein described optical filter system for its own image recording devices (photographic apparatuses or video cameras, for example).

Alternatively, the kit may comprise one or more optical filter systems already mounted on a support adaptable to image recording systems.

The kit as described above could comprise even one or more light sources at a wavelength comprised between 200 and 1.100 nm, in a particular embodiment, said light source could be a photopolymerizing lamp.

EXAMPLES

Example 1

Assay for the Determination of Light Sources Compatible with the Wearable Device of the Invention Oral mucosae of patients have been analysed by using the wearable device of the invention by lighting the mouth area to be examined with different light sources. In particular different photopolymerizing lamps available on the market, commonly utilized in dental surgery, have been used.

In table 1, reported below, it is highlighted how almost all lamps known to the inventors have revealed to be suitable to the desired use.

TABLE 1

| LAMP | PRODUCER | COMPATIBILITY |
|---|---|---|
| Allegro | Den-Mat | OK |
| Bluelight s | Mectron | OK |
| Bluephase | Ivodar-Vivadent srl | OK |
| B-Max | Tecno-Gaz industries | OK |
| Coltolux 3 | 3M | OK |
| Cybird | DXM | OK |
| Degulux soft star | Dentsply Degusta | OK |
| Deltalight | Elettronica Trasimeno | X |
| Demetron A.1 | KerrHawe | OK |
| Demetron A.2 | KerrHawe | OK |
| Demetron LC | KerrHawe | OK |
| Demi | KerrHawe | OK |
| Eliolux DLX | 3M | OK |
| Elipar 2500 | 3M | OK |
| Led demetron 1 | KerrHawe | OK |
| Mini led | SATELEC Acteongroup | OK |
| Optilux 501 | KerrHawe | OK |
| PenCure | Morita | OK |
| Poliled | Faro spa | OK |
| Poliled compact | Faro spa | OK |
| Radii | Southern Dental Industries Ltd. | OK |
| Smartlite IQ | Dentsply Caulk | OK |
| Smartlite PS | Dentsply DeTrey | OK |
| Spectrum | 3M | OK |
| Spectrum 800 | Dentsply Caulk | OK |
| Starlight p | Mectron | OK |
| Starlight pro | Mectron | OK |
| Starlight s | Mectron | OK |
| Swiss Master Light | EMS SA | X |
| T LED | ELCA Technologies | OK |
| Translux power blue | Heraeus Kulzer | OK |
| U.V.LUX F.A.6 D | Nuova Alba srl | X |
| Ultra+ | Orion | OK |
| VIP | Carbon Denit spa | OK |
| XL3000 | 3M | OK |

OK: Compatible; X: Not compatible.

Example 2

Measurement of the Transmittance Curve and Verification of the Technical Features of the Optical Filter System Made According to the Description Systems of optical filters according to the above description have been made, comprising three nanometre-controlled lens in optical glass superimposed one to another and joined by gluing with synthetic Canada balsam, the used optical glasses were commercial filters, in particular, the filters in optical glass Schott BG39, GG495 and BG23.

Figure 5:
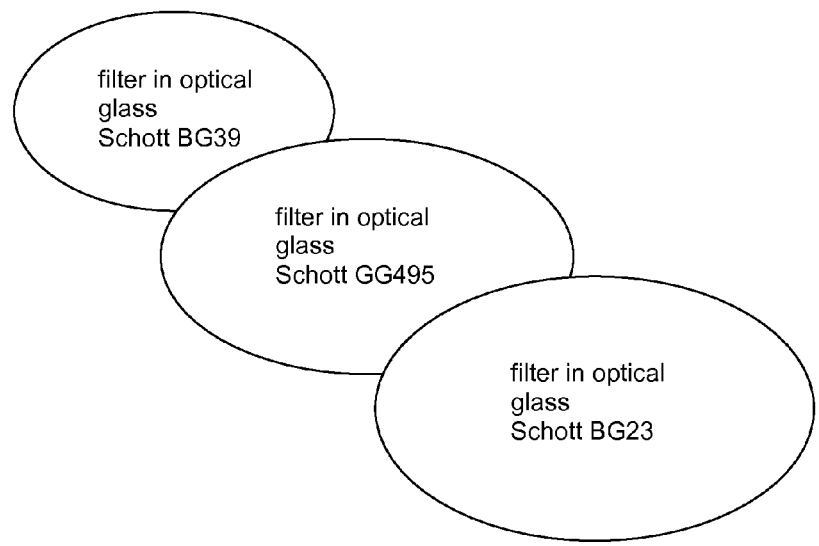
FIG. 5 is a schematization of a filter according to example 2.

FIG. 5 schematizes the realisation of the optical filter system according to the example.

The detection of the data reported below has been performed with a Shimadzu instrument model UV1601.

Figure 6:
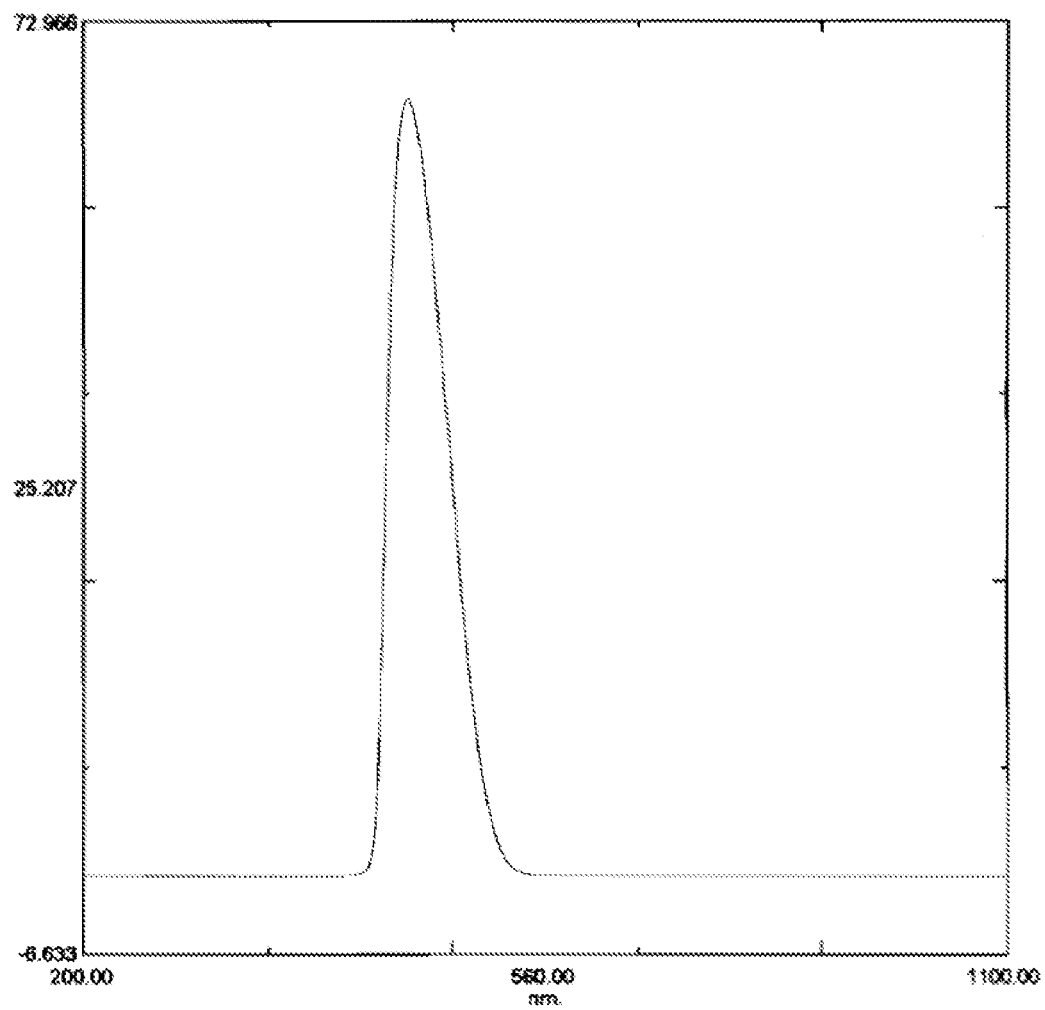
FIG. 6 is a graph representing the transmittance curve of a filter implemented according to the present invention, in a range of wavelengths comprised between 200 and 1100 nm.

The transmittance curve of a filter realised according to the present invention, in a range of wavelength comprised between 200 and 1100 nm is shown in FIG. 6.

Table 2, below, reports the raw data sampled between 200 and 1100 nm at ranges of 5 nm.

TABLE 2

| Wavelength nm. | Raw Data . . . |
|---|---|
| 200.00 | 0.000 |
| 205.00 | 0.000 |
| 210.00 | 0.000 |
| 215.00 | 0.000 |
| 220.00 | 0.000 |
| 225.00 | 0.000 |
| 230.00 | 0.000 |
| 235.00 | 0.000 |
| 240.00 | 0.000 |
| 245.00 | 0.000 |
| 250.00 | 0.000 |
| 255.00 | 0.000 |
| 260.00 | 0.000 |
| 265.00 | 0.000 |
| 270.00 | 0.000 |
| 275.00 | 0.000 |
| 280.00 | 0.000 |
| 285.00 | 0.000 |
| 290.00 | 0.000 |
| 295.00 | 0.000 |
| 300.00 | 0.000 |
| 305.00 | 0.000 |
| 310.00 | 0.000 |
| 315.00 | 0.000 |
| 320.00 | 0.000 |
| 325.00 | 0.012 |
| 330.00 | 0.000 |
| 335.00 | 0.000 |
| 340.00 | 0.012 |
| 345.00 | 0.000 |
| 350.00 | 0.000 |
| 355.00 | 0.000 |
| 360.00 | 0.000 |
| 365.00 | 0.000 |
| 370.00 | 0.000 |
| 375.00 | 0.000 |
| 380.00 | 0.000 |
| 385.00 | 0.000 |
| 390.00 | 0.000 |
| 395.00 | 0.000 |
| 400.00 | 0.000 |
| 405.00 | 0.000 |
| 410.00 | 0.000 |
| 415.00 | 0.000 |
| 420.00 | 0.000 |
| 425.00 | 0.000 |
| 430.00 | 0.012 |
| 435.00 | 0.000 |
| 440.00 | 0.000 |
| 445.00 | 0.000 |
| 450.00 | 0.000 |
| 455.00 | 0.012 |
| 460.00 | 0.037 |
| 465.00 | 0.085 |
| 470.00 | 0.171 |
| 475.00 | 0.403 |
| 480.00 | 1.465 |
| 485.00 | 6.104 |
| 490.00 | 18.567 |
| 495.00 | 36.243 |
| 500.00 | 51.794 |
| 505.00 | 60.791 |
| 510.00 | 65.112 |
| 515.00 | 66.333 |
| 520.00 | 65.637 |
| 525.00 | 63.623 |
| 530.00 | 60.718 |
| 535.00 | 56.970 |
| 540.00 | 52.588 |
| 545.00 | 47.888 |
| 550.00 | 42.834 |
| 555.00 | 37.549 |
| 560.00 | 32.227 |
| 565.00 | 27.063 |
| 570.00 | 22.266 |
| 575.00 | 17.834 |
| 580.00 | 13.892 |
| 585.00 | 10.461 |

TABLE 2-continued

| Wavelength nm. | Raw Data... |
|---|---|
| 590.00 | 7.617 |
| 595.00 | 5.347 |
| 600.00 | 3.650 |
| 605.00 | 2.417 |
| 610.00 | 1.526 |
| 615.00 | 0.928 |
| 620.00 | 0.537 |
| 625.00 | 0.305 |
| 630.00 | 0.159 |
| 635.00 | 0.073 |
| 640.00 | 0.037 |
| 645.00 | 0.012 |
| 650.00 | 0.000 |
| 655.00 | 0.000 |
| 660.00 | 0.000 |
| 665.00 | 0.000 |
| 670.00 | 0.000 |
| 675.00 | 0.000 |
| 680.00 | 0.000 |
| 685.00 | 0.000 |
| 690.00 | 0.000 |
| 695.00 | 0.000 |
| 700.00 | 0.000 |
| 705.00 | 0.000 |
| 710.00 | 0.000 |
| 715.00 | 0.000 |
| 720.00 | 0.000 |
| 725.00 | 0.000 |
| 730.00 | 0.000 |
| 735.00 | 0.000 |
| 740.00 | 0.000 |
| 745.00 | 0.000 |
| 750.00 | 0.000 |
| 755.00 | 0.000 |
| 760.00 | 0.000 |
| 765.00 | 0.000 |
| 770.00 | 0.000 |
| 775.00 | 0.000 |
| 780.00 | 0.000 |
| 785.00 | 0.000 |
| 790.00 | 0.000 |
| 795.00 | 0.000 |
| 800.00 | 0.000 |
| 805.00 | 0.000 |
| 810.00 | 0.000 |
| 815.00 | 0.000 |
| 820.00 | 0.000 |
| 825.00 | 0.000 |
| 830.00 | 0.000 |
| 835.00 | 0.000 |
| 840.00 | 0.000 |
| 845.00 | 0.000 |
| 850.00 | 0.000 |
| 855.00 | 0.000 |
| 860.00 | 0.000 |
| 865.00 | 0.000 |
| 870.00 | 0.000 |
| 875.00 | 0.000 |
| 880.00 | 0.000 |
| 885.00 | 0.000 |
| 890.00 | 0.000 |
| 895.00 | 0.000 |
| 900.00 | 0.000 |
| 905.00 | 0.000 |
| 910.00 | 0.000 |
| 915.00 | 0.000 |
| 920.00 | 0.000 |
| 925.00 | 0.000 |
| 930.00 | 0.000 |
| 935.00 | 0.000 |
| 940.00 | 0.000 |
| 945.00 | 0.000 |
| 950.00 | 0.000 |
| 955.00 | 0.000 |
| 960.00 | 0.000 |
| 965.00 | 0.000 |
| 970.00 | 0.000 |
| 975.00 | 0.000 |
| 980.00 | 0.000 |
| 985.00 | 0.000 |
| 990.00 | 0.000 |
| 995.00 | 0.000 |
| 1,000.00 | 0.000 |
| 1,005.00 | 0.000 |
| 1,010.00 | 0.000 |
| 1,015.00 | 0.000 |
| 1,020.00 | 0.000 |
| 1,025.00 | 0.000 |
| 1,030.00 | 0.000 |
| 1,035.00 | 0.000 |
| 1,040.00 | 0.000 |
| 1,045.00 | 0.000 |
| 1,050.00 | 0.000 |
| 1,055.00 | 0.000 |
| 1,060.00 | 0.000 |
| 1,065.00 | 0.000 |
| 1,070.00 | 0.000 |
| 1,075.00 | 0.000 |
| 1,080.00 | 0.000 |
| 1,085.00 | 0.000 |
| 1,090.00 | 0.000 |
| 1,095.00 | 0.000 |
| 1,100.00 | 0.000 |

As it is evident from the table, the optical filter system made is highly selective for wavelengths around 515 nm.

Example 3

Realisation of the Kit of the Invention

In order to verify the suitability of the optical filter system of the invention to the image recording, such system has been mounted on a support for Nikon filter and photographic shots have been performed (ex. FIG. 2B) with a photographic apparatus Nikon D70 equipped with lens Nikkor AF Micro 60 mm. As it is clear from the photograph in 2B (numerous photographic data are not reported herein), the optical filter system according to the present description is suitable to the use on apparatuses for the image recording and it allows the operator to record and store the observed data.

The invention claimed is:

1. A wearable device for detection of auto fluorescence of an animal biological tissue, said animal biological tissue emitting a fluorescent component at a wavelength of about 515 nm when illuminated by a light source at a wavelength comprised between 200 and 1100 nm, said wavelength comprising at least one component at about 450 nm, said device comprising:
   a frame for glasses or a visor configured for optically positioning said wearable device for a user thereof; and
   an optical filter system having at least a pair of bandpass filters and a high-pass filter and isolating, in use, said fluorescent component and excluding components in visible and UV frequencies, said optical filter system being positioned in said frame for glasses or visor and comprising at least three superimposed nanometer-controlled lenses in optical glass, wherein, said optical filter system is configured for optically rendering said fluorescent component for said user and wherein said at least three superimposed lenses comprise:
   a first lens of said at least three lenses comprising a first bandpass filter of said pair of bandpass filters, said first bandpass filter having a transmittance curve showing a peak at about 500 nm and a band width comprised between about 300 and about 700 nm;

a second lens of said at least three lenses superimposed in relation to said first lens and comprising a high-pass filter having a transmittance curve showing a plateau beyond about 540 nm; and a third lens of said at least three lenses superimposed in relation to at least said second lens and comprising a second bandpass filter of said pair of bandpass filters, said second bandpass filter having a transmittance curve showing a peak at about 465 nm and a band wideness comprised between about 300 and about 600 nm.

2. The wearable device according to claim 1, wherein said three superimposed nanometer-controlled lenses are glued together.

3. The wearable device according to claim 1, further comprising ambient light screening elements.

4. The wearable device according to claim 1, further comprising videotaping means, said videotaping means being positioned so to capture filtered images.

5. A sight correction glass comprising the wearable device according to claim 1.

6. A diagnostic kit comprising the wearable device according to claim from 1 and a marker operable for rendering a marking detectable through said wearable device.

7. The diagnostic kit according claim 6, wherein said wearable device is configured to provide a support adaptable to image taping systems.

8. The diagnostic kit according to claim 6, wherein said marker comprises a writing device using an ink comprising a fluorescent or a non-fluorescent dye detectable through said wearable device.

9. The diagnostic kit according to claim 8, further comprising a light source at a wavelength comprised between 200 and 1100 nm, said wavelength comprising at least one component at about 450 nm.

10. The diagnostic kit according to claim 9, wherein said light source is a photopolymerising lamp.

11. An optical filter system comprising:
a first optical bandpass filter comprising a first lens;
an optical high-pass filter comprising a second lens superimposed upon said first lens; and
a second optical bandpass filter comprising a third lens superimposed upon at least said second lens;
wherein said first lens, said second lens and said third lens comprise three superimposed nanometer-controlled lenses made of optical glass, and wherein:
said first optical bandpass filter has a transmittance curve showing a peak at about 500 nm and a band width comprised between about 300 and about 700 nm;
said optical high-pass filter has a transmittance curve showing a plateau beyond about 540 nm; and
said second optical bandpass filter has a transmittance curve showing a peak at about 465 nm and a band width comprised between about 300 and about 600 nm.

12. The optical filter system according to claim 11, wherein said three superimposed nanometer-controlled lenses are glued together.

13. A diagnostic kit comprising the optical filter system according to claim 11, and one or more writing devices using an ink comprising a fluorescent or a non-fluorescent dye detectable through said optical filter system.

* * * * *